US012405261B2

(12) United States Patent
Lohse et al.

(10) Patent No.: US 12,405,261 B2
(45) Date of Patent: *Sep. 2, 2025

(54) SOIL DEPTH MEASUREMENT SYSTEM AND METHOD

(71) Applicant: Kathleen A. Lohse, Pocatello, ID (US)

(72) Inventors: Kathleen A. Lohse, Pocatello, ID (US); Nicholas R. Patton, East Palo Alto, CA (US); Sarah E. Godsey, East Palo Alto, CA (US); Benjamin T. Crosby, East Palo Alto, CA (US)

(73) Assignee: Kathleen A. Lohse, Pocatello, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/090,327

(22) Filed: Dec. 28, 2022

(65) Prior Publication Data

US 2023/0160870 A1 May 25, 2023

Related U.S. Application Data

(63) Continuation of application No. 16/138,681, filed on Sep. 21, 2018, now Pat. No. 11,567,055.

(60) Provisional application No. 62/561,973, filed on Sep. 22, 2017, provisional application No. 62/561,811, filed on Sep. 22, 2017.

(51) Int. Cl.
*G01N 33/24* (2006.01)
*G01N 33/00* (2006.01)
*G01S 17/89* (2020.01)

(52) U.S. Cl.
CPC .............. *G01N 33/24* (2013.01); *G01S 17/89* (2013.01); *G01N 33/0077* (2024.05)

(58) Field of Classification Search
CPC .......... G01N 2033/0077; G01N 33/246; E02D 1/022; G01S 17/89
See application file for complete search history.

(56) References Cited

U.S. PATENT DOCUMENTS

2016/0003792 A1* 1/2016 Owens ................... G01N 33/24
  702/5
2016/0275211 A1* 9/2016 Shuler ..................... G06F 30/13

OTHER PUBLICATIONS

Ziadat, Feras M. "Prediction of soil depth from digital terrain data by integrating statistical and visual approaches." Pedosphere 20.3 (2010): 361-367. (Year: 2010).*

(Continued)

*Primary Examiner* — Lisa M Caputo
*Assistant Examiner* — Carter W Ferrell
(74) *Attorney, Agent, or Firm* — Manatt, Phelps & Phillips, LLP

(57) ABSTRACT

A soil thickness/depth determining system and method may be used to predict soil depth/thickness.

10 Claims, 6 Drawing Sheets

(56) References Cited

OTHER PUBLICATIONS

Hengl, Tomislav, et al. "SoilGrids1km—global soil information based on automated mapping." PloS one 9.8 (2014): e105992. (Year: 2014).*

Hurst, Martin D., et al. "Using hilltop curvature to derive the spatial distribution of erosion rates." Journal of Geophysical Research: Earth Surface 117.F2 (2012). (Year: 2012).

Lane, David, et al., "Introduction to Linear Regression" 2003, pp. 462-467. (Year: 2003).

Crouvi, et al., "Predicting the thickness and aeolian fraction of soils in upland watersheds of the Mojave Desert", Geoderma, vols. 195-196, 2013, pp. 94-110, ISSN 0016-7061. (Year: 2013).

Pelletier, et al. "Geomorphically based predictive mapping of soil thickness in upland watersheds." Water Resources Research 45.9 (2009). (Year: 2009).

* cited by examiner

SOIL DEPTH MEASUREMENT SYSTEM AND METHOD

PRIORITY CLAIMS/RELATED APPLICATIONS

This application is a continuation of and claims priority under 35 USC 120 to U.S. patent application Ser. No. 16/138,681 filed Sep. 21, 2018 that in turn claims the benefit under 35 USC 119(e) to U.S. Provisional Patent Application Ser. Nos. 62/561,973 and 62/561,811 both of which are filed on Sep. 22, 2017 and entitled "Soil Depth Measurement System and Method", all of which are incorporated herein by reference.

APPENDICES

Appendix A (33 pages) is a paper entitled "Predicting Soil Thickness of Soil Mantled Hillslopes"; and Appendix B (39 pages) is a paper entitled "Predicting Soil Thickness of Soil Mantled Hillslopes" both of which describe further details of the system and method for soil depth measurement and that form part of the specification and are incorporated herein by reference.

FIELD

The disclosure relates generally to a system and method for determining soil depth/thickness.

BACKGROUND

In various industries and endeavors, it is desirable to know the thickness of soil in a particular area. For example, in the constructions industry, it is often quite important to know the depth of soil (soil thickness) in a particular area. In most situations, the soil is excavated in order to determine the soil thickness, which is very costly and time consuming. Alternatively, expensive ground radar may be used to determine soil depth. Thus, the technical problem currently existing is that it is prohibitively expensive or infeasible to be able to accurately determine soil depth at a location. It is desirable to be able to determine soil thickness/depth using a technical solution and it is to this end that the disclosure is directed.

DETAILED DESCRIPTION OF ONE OR MORE EMBODIMENTS

The disclosure is particularly applicable to determining soil depth on soil mantled hillslopes as disclosed in Appendices A and B, and it is in this context that the disclosure will be described. It will be appreciated, however, that the system and method for soil determination has greater utility since the system and method may be used to determine soil depth/thickness in any area in which soil samples collected to the depth of mobile-immobile regolith boundary to define the thickness of mobile regolith may be available.

Figure 1:
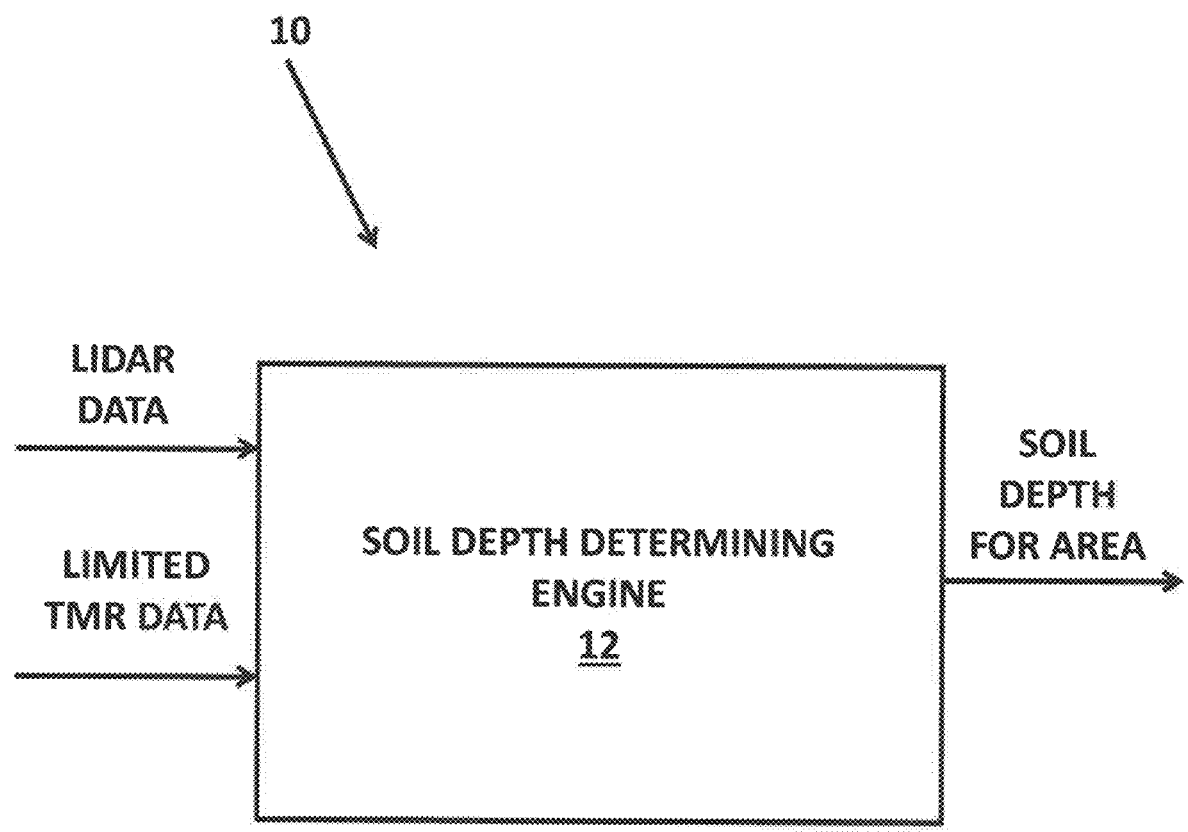
FIG. 1 illustrates an example of a system for soil depth measurement.

FIG. 1 illustrates an example of a system 10 for soil depth measurement that is a technical solution that addresses the technical problem described above. The system 10 is able to receive several inputs (without extensive excavation or the infeasible ground radar) and then programmatically and automatically generate a soil depth determination for an area. The area may be a construction site, an region of land, etc. and the system and method are not limited to the application of this system and method to any particular area as long as the area of interest is a watershed area so that the soil depth can be determined for any point in that area. In an illustrative example contained in Appendix A, the area is a soil mantled hillslope.

The system 10 may include a soil depth determining engine 12. The soil depth determining engine 12 may receive various ranging data, such as light detecting and ranging (LiDAR) data in one embodiment, and limited thickness of mobile regolith ("TMR") data and may generate soil depth data for the area using the ranging data and the TMR data. In alternative embodiments, the ranging data (and the ranging system used to generate the ranging data) and/or resolution may be other types of detecting and ranging systems and data that are known or may be developed in the future.

In one embodiment, the soil depth determining engine 12 may be a computing device that has at least one processor, memory, a display and input/output devices that may be used to receive the data shown in FIG. 1 and may generate the soil depth of the area based on the input data. For example, the soil depth determining engine 12 may be a personal computer, a tablet computer, a server computer, a cloud computing resource, a mainframe and the like. The soil depth determining engine 12 may perform a process, using the inputs shown in FIG. 1, to generate the soil depth for the area. When the system and method are being used to determine the soil depth for a particular area, the ranging data may be ranging data relevant to the particular area and the TMR data may be TMR data relevant to the particular area. It should be noted that the particular computer architecture used for the soil depth determining engine 12 is not limited since the soil depth determining engine 12 may be implemented using any known or yet to be developed computer architectures. The soil depth determining engine 12 may further include a plurality of lines of computer code/instructions that may be executed by the processor of the soil depth determining engine 12 to generate the soil depth for the area wherein the processor is thus configured to perform that process. Furthermore, the soil depth determining engine 12 may be implemented as a plurality of lines of computer code/instructions that may be distributed to a third party.

In another embodiment, the soil depth determining engine 12 may be implemented in hardware in which the hardware may be a microprocessor, microcontroller, state machine, field programmable gate array and the like. The hardware device may thus be configured to perform the process to generate the soil depth for the area.

Figure 2:
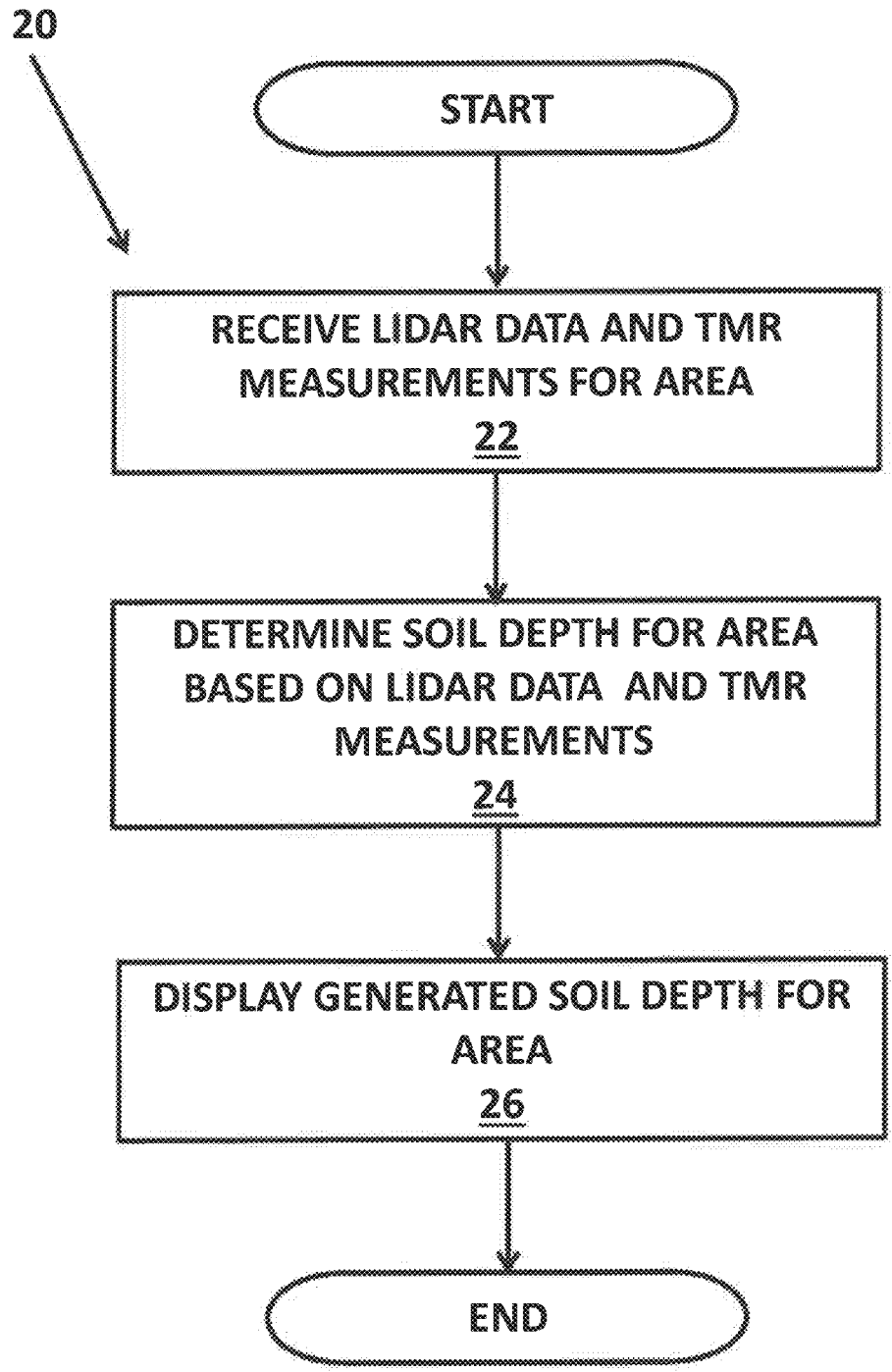
FIG. 2 illustrates a method for soil depth measurement.

FIG. 2 illustrates a method 20 for soil depth measurement. An example of an implementation of the method are contained in Appendices A and B that are incorporated herein by reference. In Appendices A and B, the area whose soil depth is being determined is a soil mantled hillslope. The disclosed method may be used in any industry in which it is important to be able to accurately determine soil depth, such as for example the construction industry that conventionally use expensive pits being dig to determine soil depth or other techniques to determine relative thickness of soil. The disclosed method accurately determines absolute thickness of soil using a technique that is unconventional, not routine and not well understood.

The method 20 shown in FIG. 2 may be implemented by the system 10 shown in FIG. 1 or it may be implemented using another system. The method may receive the ranging data, LiDAR data in one example shown in Appendix A) and the TMR data for a particular area. (22). Using these pieces of data, the method may generate the soil depth for the area (24). Two examples of the detailed steps of this process are contained in Appendix A and Appendix B that are incorporated herein by reference and form part of the specification.

Figure 3:
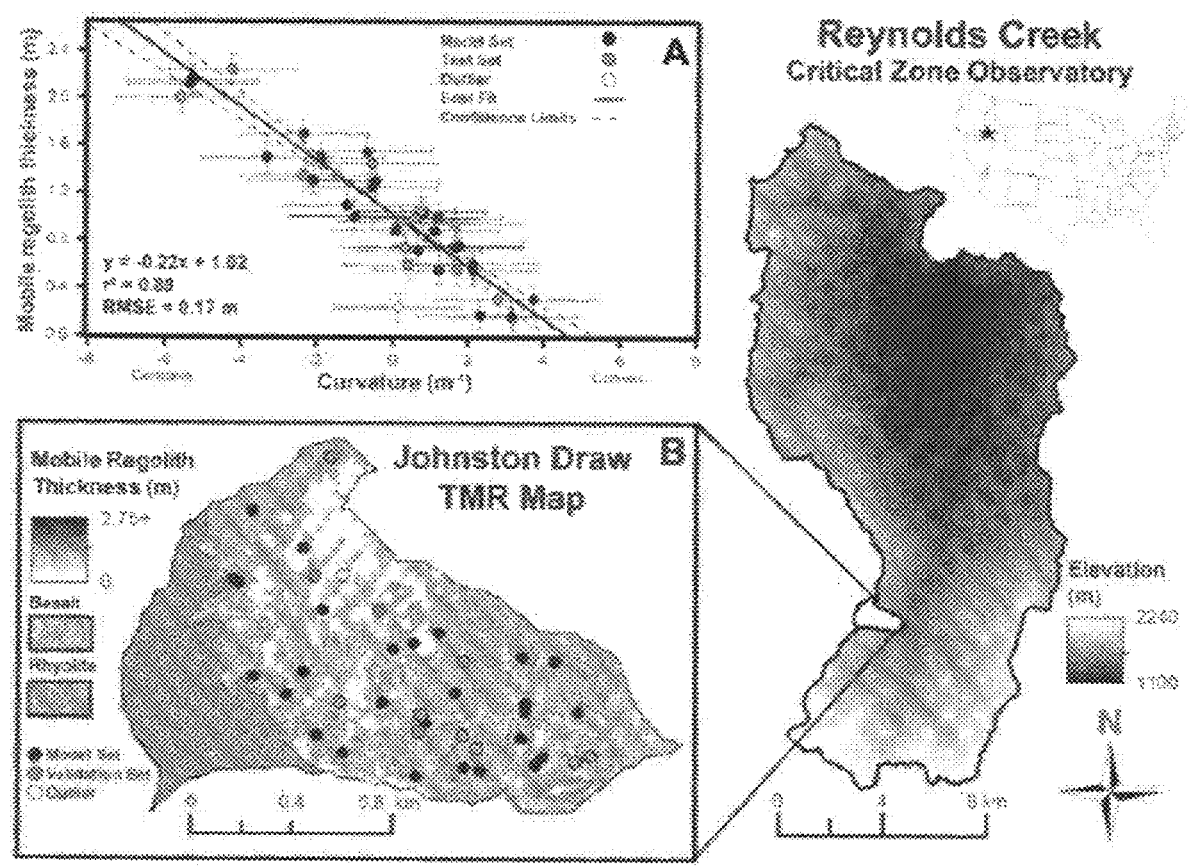
FIG. 3 illustrates mobile regolith thickness as a :function of curvature.
Figure 4:
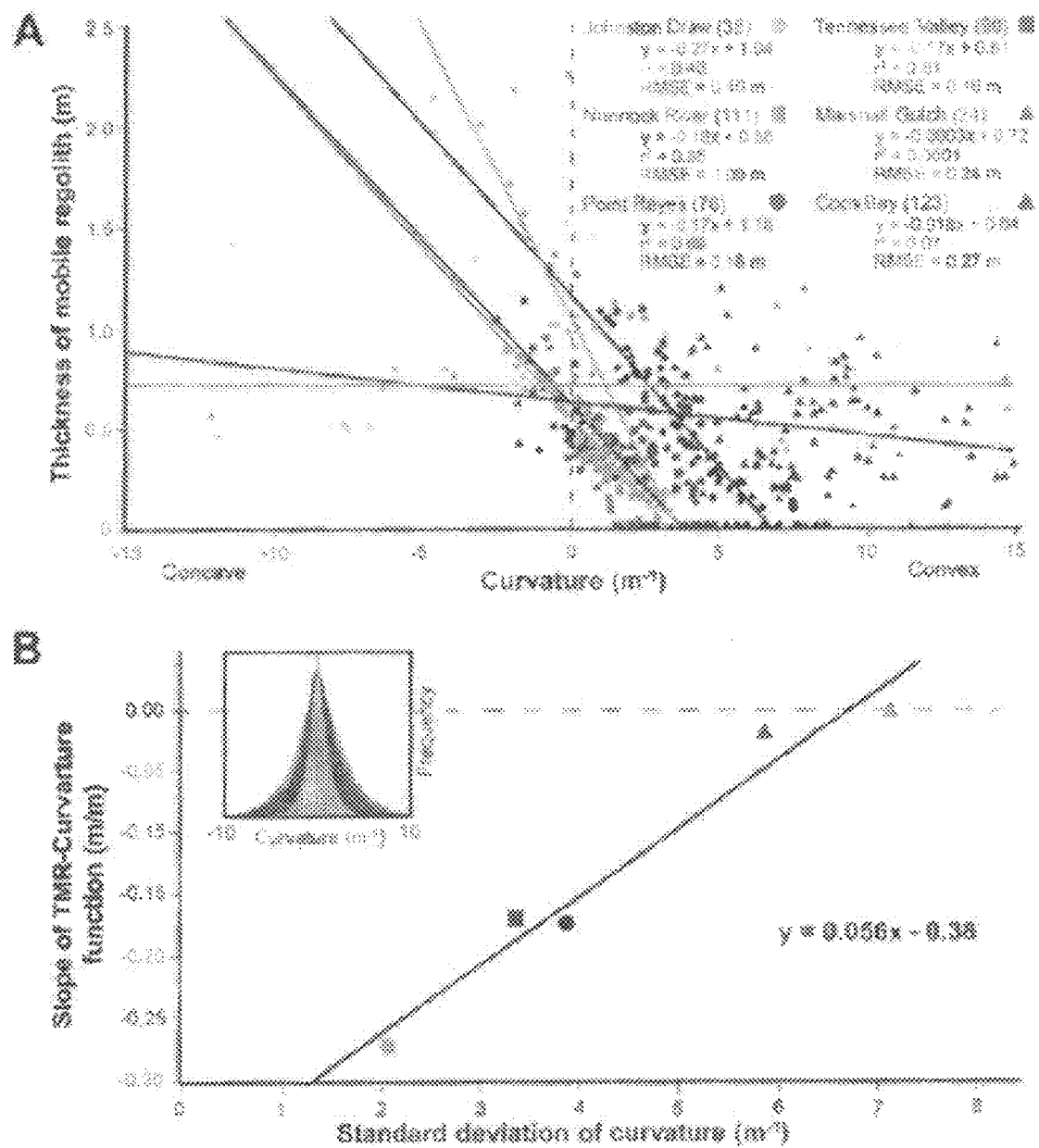
FIG. 4 illustrates evaluations of the TMR-curvature relationship for a first embodiment of the method.

In one embodiment, the soil depth may be determined using an empirical model to predict TMR (soil depth) at any location within a catchment using high-resolution LiDAR data and a limited number of existing TMR measurements. The soil depth may be used to determine TMR (soil depth) at a point (h) and the curvature about that point ($\nabla^2$):

$$h = \left(\frac{\Delta h}{\Delta \nabla^2}\right)\nabla^2 + \bar{h}$$

where $$\left(\frac{\Delta h}{\Delta \nabla^2}\right)$$

is the slope of the TMR vs $\nabla^2$ illustrated in FIG. 3 and $\bar{h}$ is the catchment average h. The slope parameter $$\left(\frac{\Delta h}{\Delta \nabla^2}\right)$$

can be estimated directly from FIG. 4 equation based on catchment SD$\nabla^2$. Because all catchments examined have a normally distributed curvature centered at O m$^{-1}$ (shown in FIG. 4B), $\bar{h}$ can be determined by measuring TMR at selected locations with planar ($\nabla^2$=O m$^{-1}$) surfaces (at least one estimate of $\bar{h}$ is required, additional pits will improve estimate and constrain uncertainty).

In more detail, chart A in FIG. 3 shows the thickness of the mobile regolith (TMR) varies as a strong inverse :function of curvature in Johnston Draw (one of the regions used). Black dots represent randomly selected build dataset (70% of sites). Gray dots represent test set to validate the model. The white dot is a location that was excluded owing to proximity to both a rock outcrop and a stream channel. A predicted TMR map (B) for the granitic portion o Johnston Draw derived from the TMR-curvature :function using a 3-m LiDAR-derived DEM. Darker shades indicate larger TMR (2.75+m) and lighter shades indicate smaller TMR (0 m). Hatched areas indicate non-granitic portions of the watershed that were not modeled.

FIG. 4 chart A shows cross-site evaluation of six catchments in which the TMR-curvature function is evaluated based on a 5-m DEM. Chart (B) is a cross-site comparison of the slope of the TMR-curvature :function and the local roughness quantified as the standard deviation in curvature. Inset shows curvature distributions based on a 5 m DEM for Johnston Draw (light blue circle), Tennessee 390 Valley (dark green square), and Marshall Gulch (orange triangle) centered on O m$^{-1}$.

Figure 5:
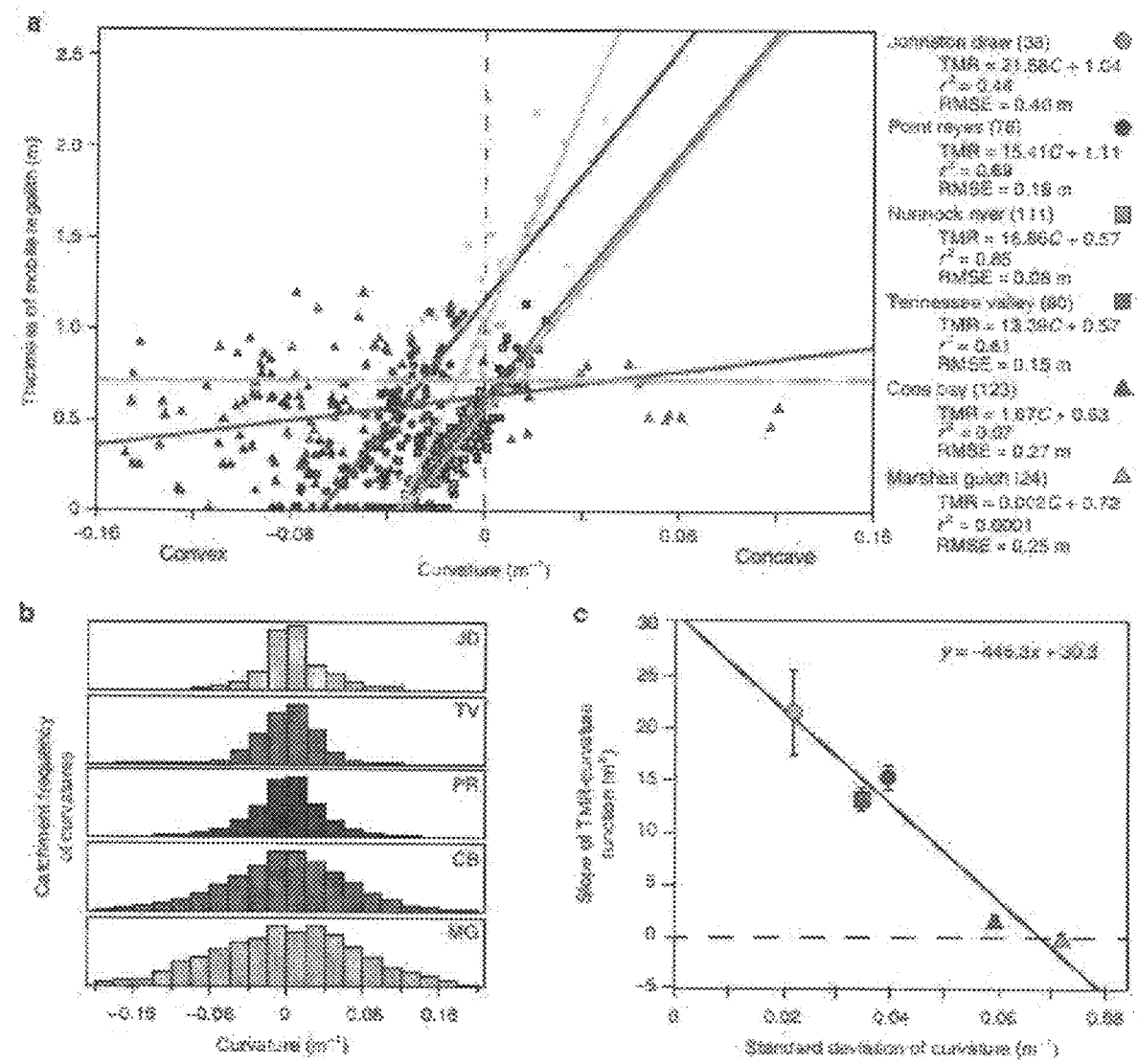
FIG. 5 illustrates evaluations of the TMR-curvature relationship for a second embodiment of the method.

In another embodiment, the soil depth may be determined using an empirical model to predict TMR (soil depth) at any location within a catchment using high-resolution LiDAR data and as few as one existing TMR measurements. The soil depth may be used to determine TMR (soil depth) at a point (h) and the curvature at that point (C):

$$h = \left(\frac{\Delta h}{\Delta C}\right)C + \bar{h}$$

where $$\left(\frac{\Delta h}{\Delta C}\right)$$

is the slope of the TMR-curvature relationship illustrated in FIG. 3a and $\bar{h}$ is the average h found within a catchment. The slope parameter $$\left(\frac{\Delta h}{\Delta C}\right)$$

can be estimated directly from the equation in FIG. 5c based on catchment $\sigma_c$. Because all catchments examined have a normally distributed curvature centered at O m$^{-1}$ (Figure Sb), $\bar{h}$ can be determined by measuring TMR at selected locations with planar (C=0 m$^{-1}$) surfaces (at least one estimate of $\bar{h}$ is required, additional pits will improve estimate and constrain uncertainty). FIG. 5 shows a cross-site evaluation of six catchments in which the thickness of the mobile regolith (TMR)-curvature (C) function is evaluated using a 5-m digital elevation model (DEM). Chart b depicts catchment curvature distributions based on a 5 m DEM centered on O m$^{-1}$. Chart c shows a cross-site comparison of the slope of the TMR-curvature :function (and associated standard error) with the local standard deviation in catchment curvature ($\sigma_c$).

The method may then generate and display the soil depth for the area (26). The process of determining the soil depth for the area is a technical solution to the above technical problem and then process has an ordered combination of processes that provides the technical solution. Furthermore, the process of determining the soil depth for the area is not accurately determinable by a human being alone.

Figure 6:
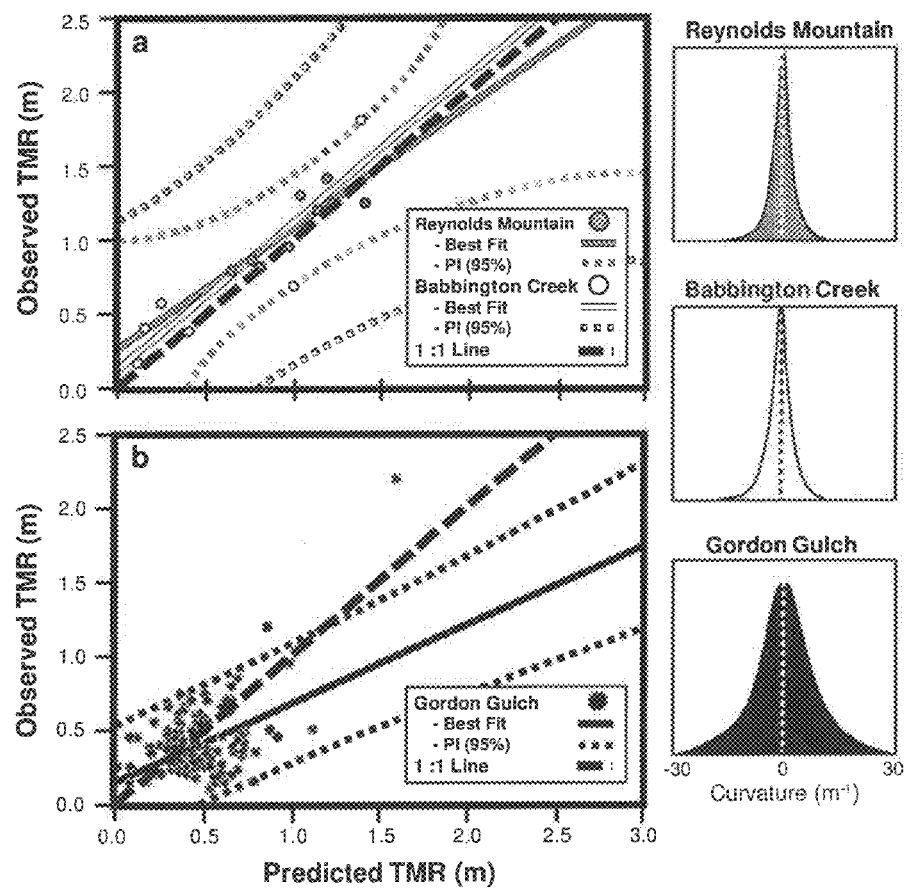
FIG. 6 shows measure versus predicted based on the soil depth measurement method.

For example, as shown in FIG. 6 (a copy of FIG. 3 in Appendix B), shows the measurement versus predicted soil depth based on the soil depth method described above. In general, the method will be more accurate when using catchments with narrow standard deviations than broader ones.

Test results of the above technique compared to known techniques or actual measured soil depth and in field measurements may be found in Appendix A and Appendix B that form part of the specification.

The foregoing description, for purpose of explanation, has been with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include and/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general-purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software, and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

What is claimed is:

1. A soil thickness determining method at any location in a catchment, the method comprising:
    gathering, by a processor of a computer system, detecting and ranging data for a location;
    digging one or more pits at the location;
    measuring, based on the one or more pits at the location, a limited number of thicknesses of a mobile regolith (TMR) for the location based on a depth of each pit;
    estimating, by the processor of the computer system, a slope of a TMR-curvature relationship ($\nabla^2$) based on a standard deviation curvature for a catchment at the location;
    determining an average height of the catchment based on the limited number of thicknesses of the TMR at the location;
    automatically determining, by the processor of the computer system, a soil thickness of the location based on the detecting and ranging data and the limited number of TMR measurements by multiplying the slope of the TMR-curvature relationship by a curvature and adding the catchment average height;
    wherein automatically determining the soil thickness further comprises applying an equation:

$$h = \left(\frac{\Delta h}{\Delta \nabla^2}\right)\nabla^2 + \overline{h}$$

where $$\left(\frac{\Delta h}{\Delta \nabla^2}\right)$$

is the slope of the TMR-curvature relationship ($\nabla^2$), h is a catchment height and $\overline{h}$ is the catchment average height; and
    displaying, on a display of the computer system, the automatically determined soil thickness.

2. The method of claim 1, wherein the limited number of TMR thickness measurements is one.

3. The method of claim 1, wherein the soil is a soil mantled hillslope.

4. The method of claim 1, wherein determining the soil thickness of the location further comprises determining the soil thickness at a construction site.

5. The method of claim 1, wherein obtaining detecting and ranging data further comprises obtaining LiDAR data.

6. A soil thickness determining system, comprising:
    a computer system having a processor and a memory and a plurality of lines of instructions, wherein the processor is configured to:
    gather detecting and ranging data for a location;
    measure, based on one or more pits dug at the location, a limited number of thicknesses of a mobile regolith (TMR) for the location based on a depth of each pit;
    estimate a slope of a TMR-curvature relationship ($\nabla^2$) based on a standard deviation curvature for a catchment at the location;
    determine an average height of the catchment based on the limited number of thicknesses of the TMR at the location;
    automatically determine, by the processor, a soil thickness of the location based on the detecting and ranging data and the limited number of TMR measurements by multiplying the slope of the TMR-curvature relationship by a curvature and adding the catchment average height;
    wherein the processor is further configured to apply an equation:

$$h = \left(\frac{\Delta h}{\Delta C}\right)C + \overline{h}$$

where $$\left(\frac{\Delta h}{\Delta C}\right)$$

is the slope of the TMR-curvature relationship, h is a catchment height and $\overline{h}$ is the average height found within the catchment; and wherein the processor is further configured display, on a display of the computer system, the automatically determined soil thickness.

7. The system of claim 6, wherein the limited number of TMR thickness measurements is one.

8. The system of claim 6, wherein the soil is a soil mantled hillslope.

9. The system of claim 6, wherein the computer system is further configured to receive a limited number of a measurement of a thickness of mobile regolith (TMR) for a construction site.

10. The system of claim 6, wherein the computer system is further configured to obtain LiDAR data.

* * * * *